United States Patent
Kunkel

[11] Patent Number: 6,079,978
[45] Date of Patent: Jun. 27, 2000

[54] MATRIX FOR DENTAL FILLINGS

[75] Inventor: Peter Kunkel, Triesen, Liechtenstein

[73] Assignee: Ivoclar AG, Schaan, Liechtenstein

[21] Appl. No.: 09/274,094

[22] Filed: Mar. 22, 1999

Related U.S. Application Data

[60] Provisional application No. 60/089,384, Jun. 15, 1998.

[30] Foreign Application Priority Data

Apr. 8, 1998 [DE] Germany .............................. 198 15 847

[51] Int. Cl.⁷ ...................................................... A61C 5/04
[52] U.S. Cl. .............................................. 433/39; 433/149
[58] Field of Search ....................... ; A61C 5/04

[56] References Cited

U.S. PATENT DOCUMENTS

| | | | |
|---|---|---|---|
| 2,629,930 | 3/1953 | Lane | 433/39 |
| 4,337,041 | 6/1982 | Harsany | 433/149 |
| 5,330,353 | 7/1994 | Wavrin | 433/39 |
| 5,421,725 | 6/1995 | Von Weissenfluh | 433/149 |

FOREIGN PATENT DOCUMENTS 38 16 501 A1  11/1989  Germany .

*Primary Examiner*—John J. Wilson
*Assistant Examiner*—Melba Bumgarner
*Attorney, Agent, or Firm*—John C. Thompson; Alan S. Korman

[57] ABSTRACT

A dental matrix for filling a lateral tooth cavity has a strip to be placed about a tooth. A wedge for applying pressure to a gap between adjacent teeth is provided. A joint connecting the wedge to the strip is provided. The wedge is moveable from a rest position into a working position by moving the wedge relative to the strip about the joint.

17 Claims, 3 Drawing Sheets

MATRIX FOR DENTAL FILLINGS

This application claims the benefit of U.S. Provisional Application Ser. No. 60/089,384, filed Jun. 15, 1998.

BACKGROUND OF THE INVENTION

The present invention relates to a matrix for filling a tooth whereby the matrix comprises a strip for surrounding the tooth for filling a lateral cavity. The matrix comprises a wedge connected to the strip for applying pressure onto the space between adjacent teeth.

Such a matrix, is for example, known from German Published Patent Application 38 16 501. Such a matrix has a strip that can be inserted into the space between two adjacent teeth. A wedge is formed on the strip and serves to force the strip onto the tooth to be filled.

Such a matrix is used to fill lateral cavities of a tooth. While for central cavities, in general, a uniform and excellent connection to the surrounding dentin is possible, the matrix strip for lateral cavities simulates the surrounding dentin and thus is designed to realize a closely fitting and gap-free filling.

It is also known to provide matrix strips of an annular design that are to be tightened by a matrix tensioning device so as to force the metallic band in a secure manner against the tooth to be filled.

However, the prior art matrix has the disadvantage that the contact of the matrix strip at the tooth to be filled in the area of the cavity is usually unsatisfactory. Especially when the dentist, in order to provide for a reliable filling, applies pressure onto the upper side of the filling, the matrix strip is easily displaced laterally so that shearing forces are present within the filling which will negatively effect the quality of the filling.

Even though a deflection of the matrix strip can be avoided by matrix tensioning, the filling result is often such that intensive finishing steps are required. Intensive finishing steps are undesirable with respect to gap formation at the border of the filling because only direct pressure onto the filling allows for a perfect, gap-free connection between filling and tooth. Also, a visual control is possible and the direct pressure application therefore is preferred.

An example for a matrix strip with matrix tensioning device is know from U.S. Pat. No. 5,330,353. In order to improve the edge connection between filling and tooth, it has been suggested to provide the matrix strip with an especially easily bendable shape. Since the tooth shape of different patients and even the tooth shape of different molars and premolars is different, such a special shaping is only a compromise.

It is therefore an object of the present invention to provide a matrix of the aforementioned kind which is especially suitable for filling lateral cavities and which combines an improved manipulation with reduced edge gap formation.

SUMMARY OF THE INVENTION

A dental matrix for filling a lateral tooth cavity according to the present invention is primarily characterized by:

A strip to be placed about a tooth;

A wedge for applying pressure to a gap between adjacent teeth;

A joint connecting the wedge to the strips;

The wedge being moveable from a rest position into a working position by moving the wedge relative to the strip about the joint.

The matrix may further comprise a securing member, wherein the joint is part of the securing member.

Advantageously, the joint is a film joint.

The joint preferably has a pivot axis extending parallel to the longitudinal extension of the strip.

The matrix may further comprise a guide member, wherein the wedge is connected to an end of the guide member and wherein the guide member is pivotable relative to the strip.

The guide member is preferably interlockingly connectable to the securing member and secures the wedge relative to the strip in the working position.

The securing member has preferably a catch facing the wedge in the rest position and the catch secures the guide member at a freely selectable side of the catch.

Adjacent to the catch a cutout is provided through which the guide member can be guided.

The wedge and the guide member in the rest position of the wedge extend in a direction of longitudinal extension of the strip and are bendable laterally about an angle of more than 180°.

Preferably, between the guide member and the securing member an elastic connecting strip is provided forming the joint, wherein the elastic connecting strip has a first length at a side connected to the securing body matching the length of the securing body and a second length at a side connected to the guide member matching the length of the guide member in the direction of the pivot axis of the joint.

Advantageously, the matrix comprises an opening for receiving a securing tie for securing the matrix against loss in a patients mouth and for providing an abutment for a dental tool.

The opening is provided in the guide member.

The wedge is symmetrical and has an insertion tip and lateral surfaces allowing abutment on either lateral side at the strip.

Advantageously, the wedge has lateral projections that in the working position of the wedge at least partially compensates a lateral projection of the securing member relative to the strip.

Expediently, the securing member has an upper forward end and the upper forward end has a button-shaped reinforcing projection.

Preferably, the securing body, the guide member, and the wedge form a unitary part made of plastic material. The plastic material is preferably polypropylene or polyethylene.

The strip is preferably a metal strip having perforations in the area of the securing member, wherein the material of the securing member penetrates the perforations.

Inventively, a matrix strip is combined with a matrix wedge in a special manner. The wedge is pivoted via the joint to a side of the strip facing away from the cavity to be filled and then can be supported at a neighboring tooth. In this manner pressure is applied especially effectively onto the strip that therefore provides an improved abutment and support action relative to the forces applied by the dentist onto the filling.

The wedge can be positioned as desired on the right or the left side of the strip depending on the position of the lateral cavity in a medial or distal position, respectively, to the right or left of the patient's mouth.

Preferably, the wedge with attached guide member can be secured or interlocked at the strip with the corresponding securing member before inserting the wedge. In this manner, a matrix is provided which can be easily manipulated and handled but is flexible with respect to different applications.

Preferably, the wedge in the working position, i.e., in the interlocked position, is located in the area of the lower edge of the strip. A lateral surface can abut with large surface area at the strip while the opposite lateral surface is supported at the neighboring tooth. In this position the neighboring tooth acts via the lateral surface and the wedge onto the matrix strip so that it rests tightly at the lateral cavity.

The joint can be embodied in any desired manner. Preferably, a connecting strip is provided between the securing member and the guide member which is in the form of a film joint and is elastic so that the interlocking of the guide member at the securing member can be realized with a certain pretension. Preferably, the securing member at its forward and upper end is provided with a button-shaped reinforcement projection. This reinforcement projection allows the dentist to apply pressure in a favorable manner onto the matrix when introducing it into the intermediate space between the teeth.

In principal, it is also possible to combine the inventive matrix with a matrix tensioning device whereby one end of the strip which is remote from the securing member is provided with a tensioning member that is interlocked and hooked at the securing body and can be tensioned by a screw.

BRIEF DESCRIPTION OF THE DRAWINGS

The object and advantages of the present invention will appear more clearly from the following specification in conjunction with the accompanying drawing, in which.

DESCRIPTION OF PREFERRED EMBODIMENTS

The present invention will now be described in detail with the aid of several specific embodiments utilizing FIGS. 1 through 3.

Figure 1:
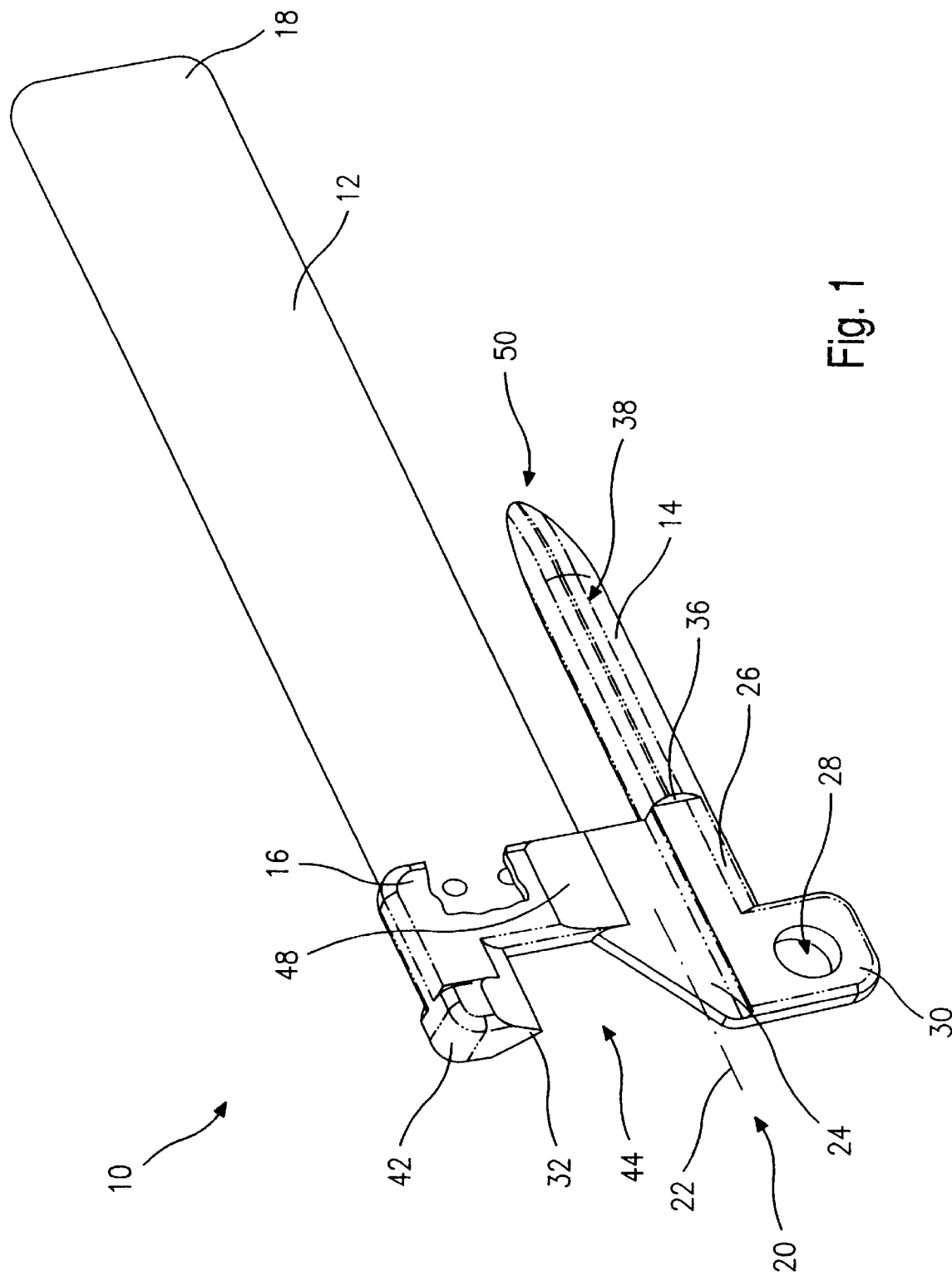
FIG. 1 shows a perspective view of the embodiment of the inventive matrix in the rest position.

The embodiment represented in FIG. 1 of a matrix 10 includes a matrix strip 12 and a wedge 14. The strip 12 is supported at a securing member 16. The strip is preferably a metal strip, and at its end 18 it is rounded. It is, in principal, also possible to employ instead of a metal strip a plastic strip.

For anchoring the strip 12 in the securing member 16, perforations on the strip in the area of the securing member are provided. The manufacture of the matrix is preferably carried out such that the strip 12 is introduced into a mold. The securing member 16 and the wedge 14 are then injection-molded about the strip 12 so that the perforations are filled with the plastic material of the securing member 16.

The securing member 16 is connected by a joint 20 to the wedge 14. The joint 20 has a schematically indicated pivot axis 22 which is substantially parallel to the strip 12 and extends to the wedge 14. In the shown embodiment, it is comprised of a connecting strip 24 made of the same plastic material as the wedge 14 and the securing member 16.

According to a modified embodiment, the joint 20 is a film joint. According to a further modified embodiment, a pin and socket joint is also possible for realizing the joint which is elastically supported at the securing member 16.

The wedge 14 is connected by a guide member 26 to the joint. The guide member 26 extends in the longitudinal direction of the wedge 14 and has a special design. The guide member 26 comprises a penetration or opening 28 into which a securing tie, for example, dental floss or a thread etc, can be inserted in order to prevent the patient from swallowing the matrix. The guide member 26 has furthermore a projection 30 designed for engaging the catch or the tip 32 of the securing member 16.

Figure 2:
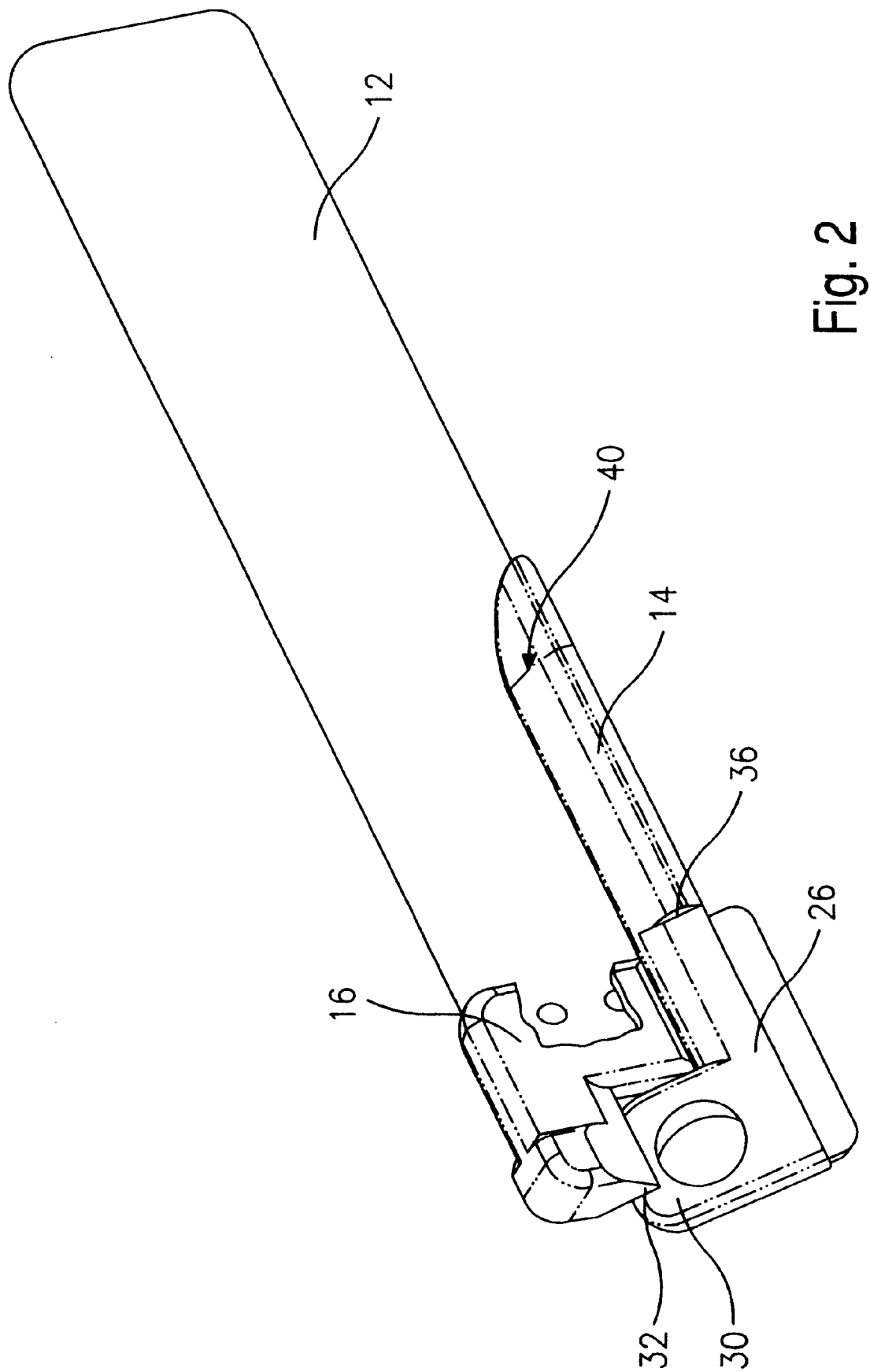
FIG. 2 shows a perspective view of the matrix according to FIG. 1 in the working position.

While FIG. 1 shows the rest position of the inventive matrix and of the wedge, FIG. 2 shows the working position. In this working position, the guide member 26 and the wedge 14 are pivoted upwardly relative to the securing member 16 and the strip 12 about the joint 20 so that the projection 30 engages behind the tip (catch) 32. The connecting strip 24 is so thin that it has sufficient elasticity to allow pivoting back into the rest position. On the other hand, it is so thick that the working position according to FIG. 2 can be maintained with sufficient safety reserves even when the matrix 10 is introduced in the space between two neighboring teeth.

Figure 3:
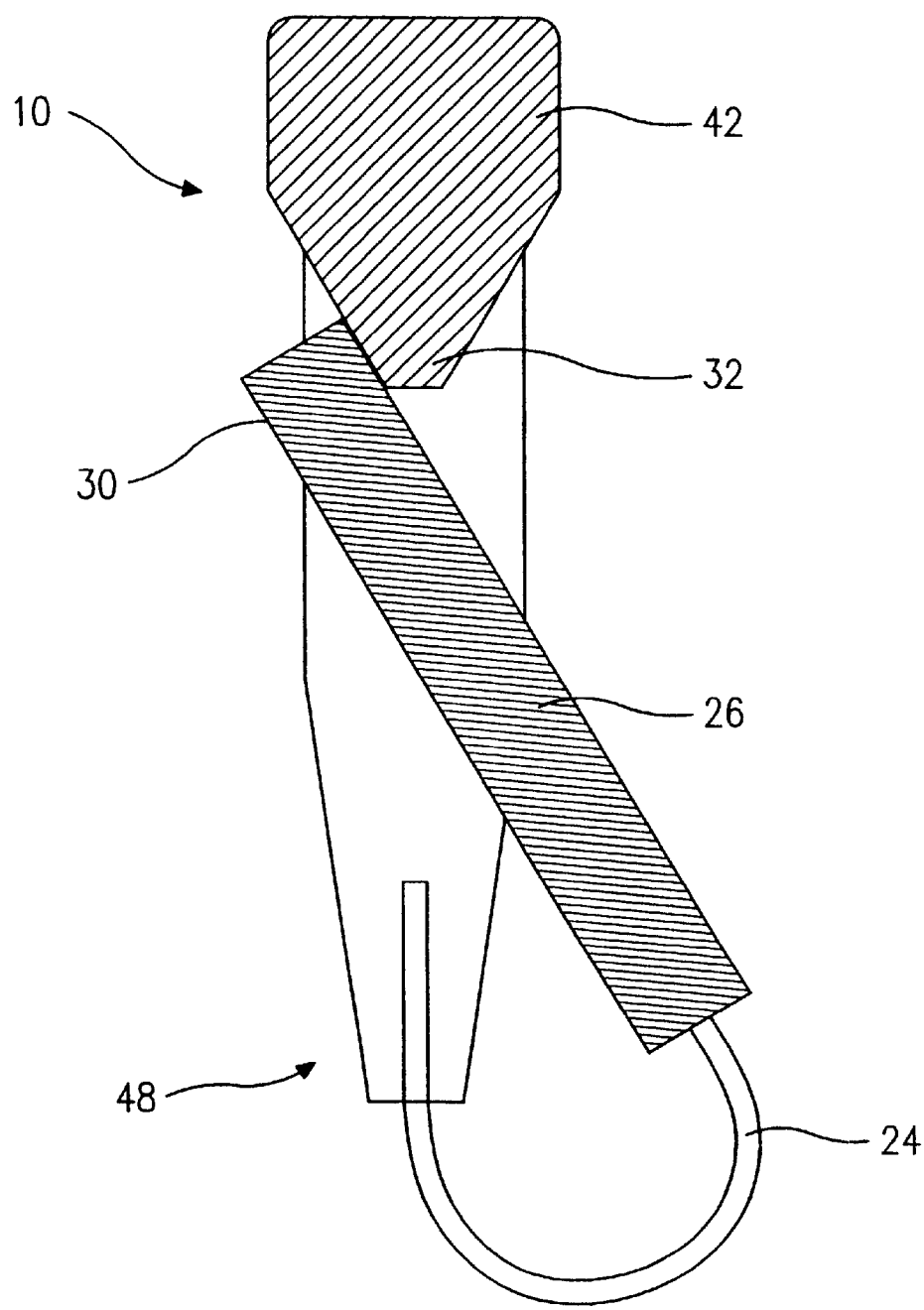
FIG. 3 shows a front view of the matrix in the embodiment according to FIG. 2.

The connecting strip 24 in the working position according to FIGS. 2 and 3 is curved or has an arc shape whereby this arc shape extends about more than 180°. Relative to the rest position the guide member 26 is pivoted by about 210° and rests with certain overlap at the catch or tip 32.

For releasing the working position and returning the matrix into the rest position, the projection 30 is pushed downwardly against the elastic effect of the connecting strip 24 so that the strip is released from the catch 32.

As can be seen in FIGS. 1 and 2, the wedge 14 has a certain amount of projecting width 36 relative to the guide member 26. This projection 36 allows a safe abutment of the wedge 14 with its lateral surface 38 at the strip 12. The opposite lateral surface 40 is then designed for abutment at the neighboring tooth.

As can be seen in FIGS. 1 and 2, the securing member 16 has a button-shaped reinforcement element 42 that projects past the width of the guide member 26 as well as of the securing member 16. Pressure can be applied from above and from the front via this reinforcement element onto the matrix 10 in the working position.

As can be seen in FIG. 1, the securing member 16 has a cutout 44 below the tip 32 which is penetrated by the guide member 26 in the working position according to FIG. 2. For a good fit and for avoiding a notching action, the connecting strip 24 is adapted, relative to the pivot axis 22 in its axial length to the guide member 26 and the securing member 16. This design allows a safe anchoring especially for a unitary construction of the securing member 16, the connecting strip 24, the guide member 26 and the wedge 14. It is understood that the securing member 16 should be so slim that pivoting of the guide member 26 is possible without problems. Preferably, it is provided with a slanted portion 48 which provides a wide transition between the width of the securing member 16 and the width of the connecting strip 24 and also allows for pivoting of the guide member 26 without canting.

The wedge 14 is of an especially suitable and favorable design. Preferably, its lateral surfaces 38 and 40 extend at an angle of approximately 60° to one another, whereby it is understood that this angle and their precise embodiment can be varied according to specific requirements.

Preferably, the wedge 14 has rounded edges and corners and tapers toward an introduction tip 50 which is also rounded on all sides.

The inventive matrix 10 is suitable for many applications since its smooth surface without inward facing corners can be easily cleaned. The matrix 10 can be sterilized and can be autoclaved.

The button-shaped reinforcement element 42 facilitates not only insertion of the wedge 14 by allowing the dentist to apply pressure with one finger, in order to introduce the wedge into the space between two teeth, but also facilitates removal of the wedge 14. The dentist can apply a tool such as pliers onto the reinforcement element and thus pull the wedge 14 out. Alternatively, it is also possible to insert a hook or a loop, for example, of dental floss, into the opening 28 for pulling out the matrix.

The present invention is, of course, in no way restricted to the specific disclosure of the specification and drawings, but also encompasses any modifications within the scope of the appended claims.

What is claimed is:

1. A dental matrix for filling a lateral tooth cavity, said matrix comprising:

a strip to be placed about a tooth;

a wedge for applying pressure to a gap between adjacent teeth; and a joint connecting said wedge to said strip, said joint having a pivot axis extending parallel to a longitudinal extension of said strip whereby the wedge is moveable from a rest position into a working position by moving said wedge relative to said strip about said joint.

2. A matrix according to claim 1, further comprising a securing member, wherein said joint is part of said securing member.

3. A matrix according to claim 2, further comprising a guide member, wherein said wedge is connected to an end of said guide member and wherein said guide member is pivotable relative to said strip.

4. A matrix according to claim 3, wherein said guide member is interlockingly connectable to said securing member and secures said wedge relative to said strip in said working position.

5. A matrix according to claim 4, wherein said securing member has a catch facing said wedge in said rest position and wherein said catch secures said guide member at a freely selectable side of said catch.

6. A matrix according to claim 5, wherein adjacent to said catch a cutout is provided though which said guide member can be guided.

7. A matrix according to claim 3, wherein said wedge and said guide member in a rest position of said wedge extend in a direction of longitudinal extension of said strip and are bendable laterally about an angle of more than 180°.

8. A matrix according to claim 3, wherein between said guide member and said securing body an elastic connecting strip is provided forming said joint, wherein said elastic connecting strip has a first length at a side connected to said securing member matching a length of said securing member and a second length at a side connected to said guide member matching a length of said guide member in a direction of said pivot axis of said joint.

9. A matrix according to claim 3, comprising an opening for receiving a securing tie for securing said matrix against loss in a patient's mouth and for providing an abutment for a dental tool.

10. A matrix according to claim 9, wherein said opening is provided in said guide member.

11. A matrix according to claim 2, wherein said wedge is symmetrical and has an insertion tip and lateral surfaces allowing abutment on either lateral side at said strip.

12. A matrix according to claim 11, wherein said wedge has lateral projection.

13. A matrix according to claim 2, wherein said securing member has an upper forward end and wherein said upper forward end has a button-shaped reinforcing projection.

14. A matrix according to claim 2 further comprising a guide member, wherein said wedge is connected to an end of said guide member, and wherein said securing body, said guide member, and said wedge form a unitary part made of plastic material.

15. A matrix according to claim 14, wherein said plastic material is polypropylene or polyethylene.

16. A matrix according to claim 2, wherein said strip is a metal strip having perforations in the area of said securing member, wherein the material of said securing member penetrates said perforations.

17. A matrix according to claim 1, wherein said joint is a film joint.

* * * * *